(12) United States Patent
Cheung et al.

(10) Patent No.: US 9,465,893 B2
(45) Date of Patent: Oct. 11, 2016

(54) BIOFEEDBACK FOR PROGRAM GUIDANCE IN PULMONARY REHABILITATION

(75) Inventors: Amy Oi Mee Cheung, Eindhoven (NL); Maryam Atakhorrami, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 880 days.

(21) Appl. No.: 13/518,075

(22) PCT Filed: Nov. 17, 2010

(86) PCT No.: PCT/IB2010/055227
§ 371 (c)(1),
(2), (4) Date: Jun. 21, 2012

(87) PCT Pub. No.: WO2011/080603
PCT Pub. Date: Jul. 7, 2011

(65) Prior Publication Data
US 2013/0116807 A1    May 9, 2013

Related U.S. Application Data

(60) Provisional application No. 61/290,342, filed on Dec. 28, 2009.

(51) Int. Cl.
*G06F 17/00* (2006.01)
*G06F 17/40* (2006.01)
*G06F 19/00* (2011.01)

(52) U.S. Cl.
CPC ........... *G06F 17/40* (2013.01); *G06F 19/3481* (2013.01); *G06F 19/3406* (2013.01)

(58) Field of Classification Search
CPC .................... A61B 5/087; G06F 19/3481
USPC .......................................... 463/36
See application file for complete search history.

(56) References Cited

U.S. PATENT DOCUMENTS

| | | | |
|---|---|---|---|
| 5,706,822 A | 1/1998 | Khavari | |
| 5,960,403 A | 9/1999 | Brown | |
| 6,159,147 A | 12/2000 | Lichter | |
| 6,626,800 B1 | 9/2003 | Casler | |
| 8,827,870 B2 * | 9/2014 | Dyer et al. | 482/9 |

(Continued)

FOREIGN PATENT DOCUMENTS

| | | |
|---|---|---|
| CN | 1836626 A | 9/2006 |
| CN | 101181156 A | 5/2008 |

(Continued)

*Primary Examiner* — Reginald Renwick
(74) *Attorney, Agent, or Firm* — Michael W. Haas

(57) ABSTRACT

A system (200) for providing an exercise training plan for a patient is provided. The system includes a sensor (202, 204, 206, 208, 210, 212), and a processor (214) operatively connected to the at least one sensor. The sensor measures physiological parameter of the patient. The processor is configured to: a) receive health information data representative of patient information and patient symptoms; b) receive physiological data from the at least one sensor; c) devise the exercise training plan for the patient based on the health information data and the physiological data; d) monitor the physiological data, during the exercise training of the patient to determine if the physiological data is within a predetermined range; and e) modify the exercise training plan for the patient if the physiological data is outside the predetermined range.

17 Claims, 3 Drawing Sheets

(56) References Cited

U.S. PATENT DOCUMENTS

| | | |
|---|---|---|
| 2003/0140925 A1 | 7/2003 | Sapienza |
| 2006/0281976 A1 | 12/2006 | Juang |
| 2008/0076637 A1 | 3/2008 | Gilley |
| 2008/0096728 A1 | 4/2008 | Foley |
| 2009/0047645 A1* | 2/2009 | Dibenedetto et al. ........ 434/258 |
| 2009/0177097 A1* | 7/2009 | Ma et al. .................... 600/500 |
| 2009/0253554 A1* | 10/2009 | McIntosh ............... A63B 21/00 482/4 |
| 2010/0022909 A1 | 1/2010 | Padiy |
| 2010/0113894 A1 | 5/2010 | Padiy |

FOREIGN PATENT DOCUMENTS

| | | | |
|---|---|---|---|
| EP | 0176277 | A2 | 4/1986 |
| EP | 1510175 | A1 | 3/2005 |
| JP | H09238911 | A | 9/1997 |
| JP | 2002224053 | A | 8/2002 |
| JP | 2003000573 | A | 1/2003 |
| JP | 2004157596 | A | 6/2004 |
| JP | 2006263002 | A | 10/2006 |
| JP | 2009169673 | A | 7/2009 |
| JP | 2010155755 | A | 7/2010 |
| WO | WO2008068665 | A1 | 6/2008 |
| WO | WO2008078271 | A1 | 7/2008 |
| WO | WO2008110947 | A1 | 9/2008 |
| WO | WO2009107009 | A2 | 9/2009 |
| WO | WO2009141780 | A1 | 11/2009 |
| WO | WO2010082102 | A2 | 7/2010 |
| WO | WO2010103436 | A1 | 9/2010 |
| WO | WO2010116297 | A1 | 10/2010 |

* cited by examiner

BIOFEEDBACK FOR PROGRAM GUIDANCE IN PULMONARY REHABILITATION

CROSS-REFERENCE TO RELATED APPLICATIONS

This patent application claims the priority benefit under 35 U.S.C. §371 of international patent application no. PCT/IB2010/055227, filed Nov. 17, 2010, which claims the priority benefit under 35 U.S.C. §119(e) of U.S. Provisional Application No. 61/290,342 filed on Dec. 28, 2009, the contents of which are herein incorporated by reference.

BACKGROUND OF THE INVENTION

1. Field of the Disclosure

The present invention relates to a computer implemented method and a system for providing exercise training plan for a patient.

2. Description of the Related Art

Chronic Obstructive Pulmonary Disease (COPD) is a respiratory disease that is characterized by inflammation of the airways. It is further characterized by an airflow limitation that is not fully reversible. The airflow limitation is both progressive and associated with an abnormal inflammatory response of the lungs to noxious particles or gases. Symptoms of COPD may include coughing, wheezing, and the production of mucus and the degree of severity can, in part, be viewed in terms of the volume and color of secretions.

Pulmonary rehabilitation is a form of treatment for a COPD patient. The pulmonary rehabilitation may include, for example, exercise training, nutrition (weight management), education, psychological and social support, and/or medical management. The exercise training not only maintains, but also improves, the physical capacity of the COPD patient.

Most exercise training plans are devised based on patient information and symptoms. The patient information may include patient's gender, age, weight, smoking history, and height. The patient symptoms may include dyspnea (or shortness of breath), cough, wheezing, mucus or sputum production, chest tightness, and fatigue. However, the patient information and symptoms only offer a limited information that is used to generate a suitable exercise training plan. Therefore, the exercise training plan devised based on the patient information and symptoms may not always be optimal for the patient (i.e., may not be tailored to an individual's health status).

Further, the outcome of these exercise training sessions are measured via a set of questionnaires. For example, after the exercise training, a questionnaire such as the Borg scale questionnaire, which consists of a scale from 1 to 10 to quantify breathlessness, is used to determine the patient condition (i.e., after exercise training). However, these questionnaires are highly subjective, and rely on memory recall, which may be demanding for the elderly patients. Thus, the measure of outcome of these exercise training sessions is rather subjective.

SUMMARY OF THE INVENTION

Accordingly, it is an object of the present invention to provide a computer implemented method for providing an exercise training plan for a patient that overcomes the shortcomings of conventional techniques. This object is achieved according to one embodiment of the present invention by providing a computer implemented method that includes a computer system comprising a processor configured to execute a computer programs module. The method includes receiving in one or more processors health information data from the patient, the health information data representative of patient information and/or patient symptoms; measuring physiological parameters of the patient with the at least one sensor to gather physiological data; executing, on the one or more processors of the computer system, one or more computer program modules configured to devise the exercise training plan for the patient based on the health information data and the physiological data; monitoring the physiological data during exercise training of the patient, to determine if the physiological data is within a predetermined range; and executing, on the one or more processors of the computer system, one or more computer program modules configured to modify the exercise training plan for the patient if the physiological data is outside the predetermined range.

Another aspect of the present invention provides a system for providing an exercise training plan for a patient. The system includes at least one sensor, and at least one processor operatively connected to the at least one sensor. The sensor is configured to measure physiological parameters of the patient to gather physiological data. The processor is configured to: a) receive health information data from the patient, the health information data representative of patient information and patient symptoms; b) receive the physiological data from the at least one sensor; c) devise the exercise training plan for the patient based on the health information data and the physiological data; d) monitor the physiological data, during the exercise training of the patient, to determine if the physiological data is within a predetermined range; and e) modify the exercise training plan for the patient if the physiological data is outside the predetermined range.

Another aspect of the present invention provides a system for providing an exercise training plan for a patient. The system includes at least one sensor, and at least one processor operatively connected to the at least one sensor. The sensor is configured to measure physiological parameters of the patient to gather physiological data. The processor is configured to: a) receive health information data from the patient, the health information data representative of patient information and patient symptoms; b) receive the physiological data from the at least one sensor; c) devise the exercise training plan for the patient based on the health information data and the physiological data; d) monitor the physiological data, during the exercise training of the patient; and e) modify the exercise training plan based on the physiological data.

These and other aspects of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. It shall also be appreciated that the features of one embodiment disclosed herein can be used in other embodiments disclosed herein.

Figure 1A:
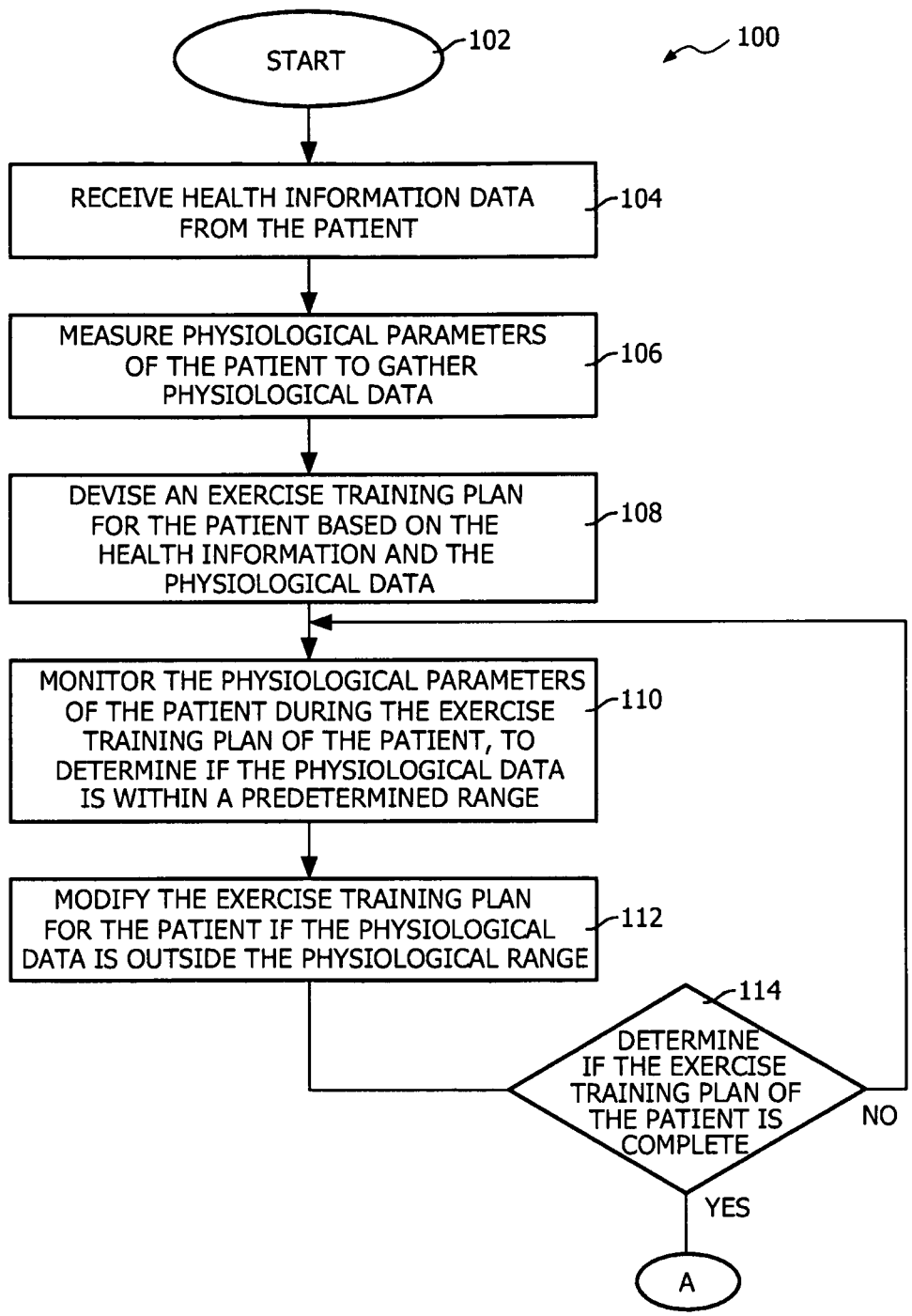
FIGS. 1A and 1B show a flow chart illustrating a computer implemented method for providing an exercise training plan for a patient in accordance with an embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

DETAILED DESCRIPTION OF EXEMPLARY EMBODIMENTS

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1B:
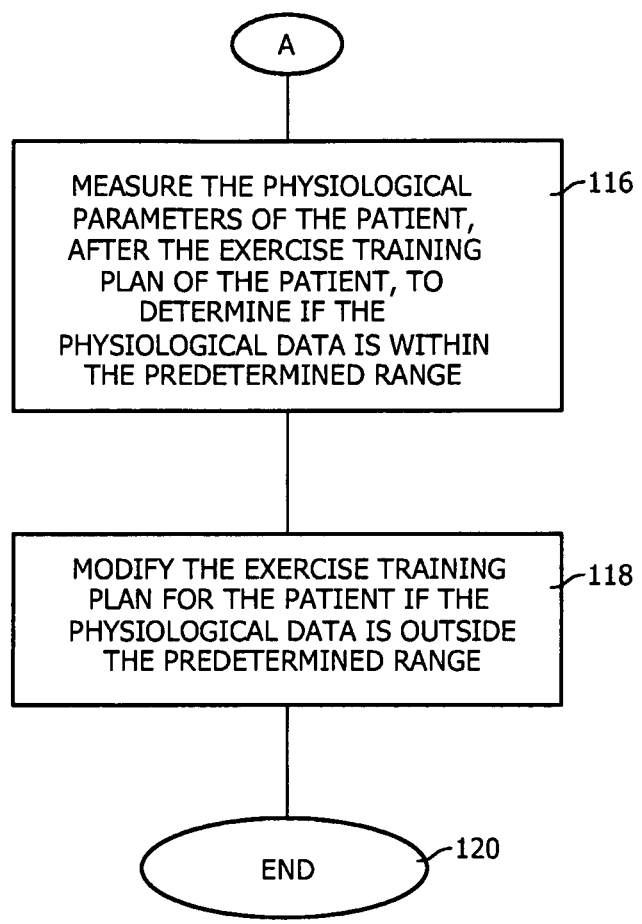

FIGS. 1A and 1B show a flow chart illustrating a computer implemented method 100 for providing an exercise training plan for a patient in accordance with an embodiment of the present invention.

Before devising the exercise training plan for the patient, physiological parameters of the patient are measured and health information data (i.e., patient information and/or patient symptoms) of the patient is obtained. The physiological parameters of the patient together with the health information data of the patient are then used to devise an appropriate exercise training plan for the patient.

During the exercise training plan, the physiological parameters are monitored to determine if the physiological data is within a predetermined range. If the physiological data is not within a predetermined range, the exercise training plan may be modified accordingly (e.g., lower or higher intensity exercise training plan; or shorter or longer duration exercise training plan). Therefore, the patient's physiological data may be used to guide the exercise training plan, resulting in a more individualized exercise training plan.

By providing a tailored or an individualized exercise training plan for the patient, the exercise training and outcome may be optimized. In one embodiment, computer implemented method 100 is also configured to assess the patient health status using the physiological data that is taken after exercise training plan is complete.

Computer implemented method 100 is implemented in a computer system comprising one or more processors 214 (as shown in and described with reference to FIG. 2) configured to execute one or more computer programs modules. Method 100 begins at procedure 102. At procedure 104, health information data of the patient is received by one or more processors 214 from the patient (or healthcare personnel (caregiver)). In one embodiment, the patient (or healthcare personnel) may manually input the health information data into a processor 214 (as shown in and described with reference to FIG. 2) and/or a data storage device 216 (as shown in and described with reference to FIG. 2) using an user interface 218 (as shown in and described with reference to FIG. 2). In one embodiment, processor 214 can comprise either one or a plurality of processors therein.

In one embodiment, the health information data is representative of patient information and patient symptoms. In one embodiment, the patient information may include patient's gender, patient's age, patient's weight, patient's smoking history, patient's height, or any combination thereof. In one embodiment, the patient symptoms may include dyspnea (or shortness of breath), cough, wheezing, mucus or sputum production, chest tightness, fatigue, or any combination thereof.

At procedure 106, physiological parameters of the patient are measured to gather physiological data. In one embodiment, the physiological parameters may include physical activity, respiration rate, amount of oxygen carried by red blood cells, heart rate, temperature, volume of air inspired and expired by the lungs, or any combination thereof.

In another embodiment, the physiological parameters may include physical activity, respiration rate, amount of oxygen carried by red blood cells, heart rate, or any combination thereof. In other words, in one embodiment, the temperature and the volume of air inspired and expired by the lungs may be excluded as they (i.e., the temperature and the volume of air inspired and expired by the lungs) may not provide valuable information related to the pulmonary rehabilitation.

In one embodiment, the physiological parameters may be measured during exercise testing (e.g., a six-minute walk test that is generally used to evaluate the exercise capacity of the patient), or exercise training (e.g., cycling, treadmill, or weight training). In one embodiment, the six-minute walk test is performed by using two cones (that are separated by a distance of, for example, thirty meters), and a stopwatch.

In one embodiment, the physiological parameters measured during exercise testing are not used in real time to modify the exercise training program. Instead, in one embodiment, the physiological parameters measured during exercise testing are used offline once the current exercise training program/session has ended.

In one embodiment, the physical activity of the patient is measured using an activity monitor 202 (as shown in and described with reference to FIG. 2). In one embodiment, the physical activity is measured in arbitrary acceleration units (AAU). In one embodiment, the respiration rate of the patient is measured using a respiration rate sensor 204 (as shown in and described with reference to FIG. 2). In one embodiment, the amount of oxygen carried by red blood cell (or amount of oxygen attached to the hemoglobin cell in the circulatory system) of the patient is measured using a $SpO_2$ sensor 206 (as shown in and described with reference to FIG. 2). In one embodiment, the heart rate of the patient is measured using a heart rate monitor 208 (as shown in and described with reference to FIG. 2). In one embodiment, the temperature of the patient is measured using a temperature sensor 210 (as shown in and described with reference to FIG. 2). In one embodiment, the volume of air inspired and expired by the lungs of the patient is measured using an airway obstruction measuring device 212 (as shown in and described with reference to FIG. 2).

Figure 2:
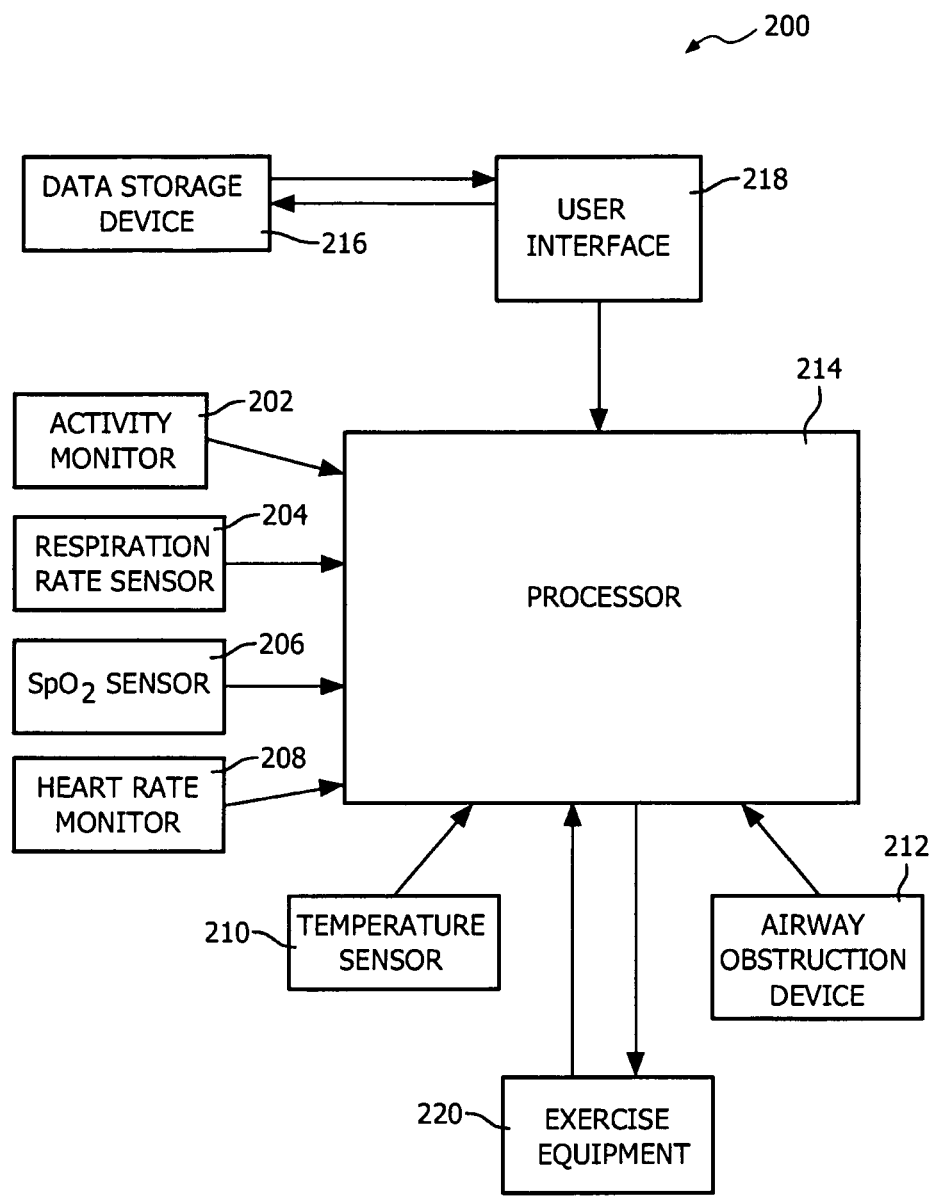
FIG. 2 shows a system for providing an exercise training plan for a patient in accordance with an embodiment of the present invention.

In system 200 shown in FIG. 2, separate sensors are used to measure each physiological parameter. However, it is contemplated, that a single sensor may be used to measure two or more physiological parameters as explained below.

For example, in one embodiment, a single sensor may be used to measure the physical activity, the heart rate and the respiration rate of the patient. Alternatively, in another embodiment, the physical activity, the heart rate and the respiration rate of the patient may be measured using separate sensors as described in system 200 (as shown in FIG. 2).

For example, in one embodiment, a single sensor may be used to measure the heart rate and the amount of oxygen carried by red blood cell (or amount of oxygen attached to the hemoglobin cell in the circulatory system) of the patient. Alternatively, in another embodiment, the amount of oxygen carried by red blood cell (or amount of oxygen attached to the hemoglobin cell in the circulatory system) of the patient, and the heart rate may be measured using separate sensors as described in system 200 (as shown in FIG. 2).

For example, in one embodiment, a single sensor may be used to measure the temperature of the patient, the respiration rate of the patient, and the physical activity of the patient. In such an embodiment, the temperature sensor may include a microphone to measure the respiration rate of the patient, and/or a one-axis, a two-axis, or a three-axis accelerometer to measure both the respiration rate and the physical activity of the patient. Alternatively, in another embodiment, the temperature of the patient, the respiration rate of the patient, and the physical activity of the patient is measured using separate sensors as described in system 200 (as shown in FIG. 2).

At procedure 108, processor 214 (as shown in and described with reference to FIG. 2) is configured to execute one or more computer program modules to devise an exercise training plan for the patient based on the health information data and the physiological data.

At procedure 110, processor 214 (as shown in and described with reference to FIG. 2) is configured to monitor the physiological data, during the exercise training plan of the patient, to determine if the physiological data is within a predetermined range.

In one embodiment, the predetermined range is patient dependent. In one embodiment, as the predetermined range is patient dependent, the predetermined range is a percentage change (e.g., at least 10%) relative to the last exercise training session.

At procedure 112, processor 214 (as shown in and described with reference to FIG. 2) is configured to execute one or more computer program modules to modify the exercise training plan for the patient if the physiological data are outside the predetermined range. As noted above, in one embodiment, the processor 214 can comprise either one or a plurality of processors therein.

In one embodiment, the exercise training plan for the patient is modified by increasing or decreasing the intensity of the exercise training. In another embodiment, the exercise training plan for the patient is modified by increasing or decreasing the duration of the exercise training. In yet another embodiment, the exercise training plan of the patient is modified by increasing or decreasing the intensity of the exercise training, and increasing or decreasing the duration of the exercise training.

At procedure 114, processor 214 (as shown in and described with reference to FIG. 2) is configured to determine whether the (devised) exercise training plan of the patient is complete.

In one embodiment, an exercise device or equipment 220 may be directly connected to processor 214. In such an embodiment, exercise device or equipment 220 may be configured to send a signal to the processor 214 that the (devised) exercise training plan of the patient is complete. Also, in such an embodiment, the exercise device or equipment 220 may be connected to processor 214 over a wired or wireless network, for example.

In another embodiment, the patient or healthcare personnel may manually input information that the (devised) exercise training plan of the patient is complete into processor 214 using user interface 218.

If the (devised) exercise training plan of the patient is complete, then method 100 proceeds to procedure 116. Otherwise, method 100 returns to procedure 110 where the physiological parameters of the patient, during the exercise training plan of the patient, are monitored to determine if the physiological data is within a predetermined range.

At procedure 116, processor 214 (as shown in and described with reference to FIG. 2) is configured to measure the physiological data, after the exercise training plan of the patient is complete, to determine if the physiological data is within the predetermined range. At procedure 118, processor 214 (as shown in and described with reference to FIG. 2) is configured to execute one or more computer program modules to modify the exercise training plan for the patient if the physiological data are outside the predetermined range.

Processor 214 may generate a signal that provides information on the exercise training plan. The processor may be connected to a printer, a graphical user interface or other output device that can communicate the information to the patient or health care provider. The printer or the graphical user interface may be a separate device or integrated into user interface 218. As noted above, in one embodiment, the exercise training plan for the patient is modified by increasing or decreasing the intensity of the exercise training. In another embodiment, the exercise training plan for the patient is modified by increasing or decreasing the duration of the exercise training. In yet another embodiment, the exercise training plan of the patient is modified by increasing or decreasing the intensity of the exercise training, and increasing or decreasing the duration of the exercise training. Method 100 ends at procedure 120.

In one embodiment, procedures 102-120 can be performed by one or more computer program modules that can be executed by one or more processors 214.

System 200 for providing an exercise training plan for a patient in accordance with an embodiment of the present invention is shown in FIG. 2. The system may include activity monitor 202, respiration rate sensor 204, $SpO_2$ sensor 206, heart rate monitor 208, temperature sensor 210, airway obstruction measuring device 212, processor 214, data storage device 216, and user interface 218. In one embodiment, system 200 may include exercise equipment/device 220. In one embodiment, processor 214 can comprise either one or a plurality of processors therein. In one embodiment, processor 214 can be a part of or forming a computer system.

Activity monitor 202 is configured to detect body movements of the patient such that a signal from the activity monitor is correlated to the level of a patient's physical activity. In one embodiment, activity monitor 202 may include an accelerometer. In one embodiment, the accelerometer may be a three-axis accelerometer. Such an accelerometer may include a sensing element that is configured to determine acceleration data in at least three axes. For example, in one embodiment, the three-axis accelerometer may be a three-axis accelerometer (i.e., manufacturer part number: LIS3L02AQ) available from STMicroelectronics.

In another embodiment, activity monitor 202 may be a piezoelectric sensor. The piezoelectric sensor may include a piezoelectric element that is sensitive to body movements of the patients. In one embodiment, the activity monitor 202 may be positioned, for example, at the thorax of the patient or at the abdomen of the patient.

In one embodiment activity monitor 202 may be directly connected to processor 214. In such an embodiment, the activity monitor may be connected to the processor over a wired or wireless network, for example. It is also contemplated that activity monitor 202 may be connected to processor 214 via data storage device 216.

In one embodiment, respiration rate sensor 204, which is configured to measure the respiration pattern of the patient, may include an accelerometer or a microphone. In one embodiment, the accelerometer may be a three-axis accelerometer. For example, in one embodiment, the three-axis accelerometer may be a three-axis accelerometer (i.e., manufacturer part number: LIS3L02AQ) available from STMicroelectronics.

In one embodiment, a microphone is constructed and arranged to receive sound of inspiration of the patient in order to determine the respiration rate of the patient. In one embodiment, respiration rate sensor 204 may be a Respiband™ available from Ambulatory Monitoring, Inc. of Ardsley, N.Y. In one embodiment, the respiration rate sensor 204 may include a chest band and a microphone as described in U.S. Pat. No. 6,159,147, hereby incorporated by reference. In such an embodiment, the chest band may be placed around a patient's chest to measure the patient's respiration rate, for example.

In one embodiment respiration rate sensor 204 may be directly connected to processor 214. In such an embodiment, the respiration rate sensor may be connected to the processor over a wired or wireless network, for example. It is also contemplated that respiration rate sensor 204 may be connected to processor 214 via data storage device 216.

In one embodiment, the amount of oxygen carried by the red blood cells (or amount of oxygen attached to the hemoglobin cell in the circulatory system) of the patient is measured using a $SpO_2$ sensor 206. In one embodiment, $SpO_2$ sensor 206 may be configured to measure the amount of oxygen carried by the red blood cells, and heart rate of the patient. In one embodiment, the $SpO_2$ sensor is electronic and electronically inputs the $SpO_2$ data into processor 214. It is also contemplated that the $SpO_2$ sensor may be connected to the processor via data storage device 216.

In one embodiment, $SpO_2$ sensor 206 is a portable $SpO_2$ sensor. For example, in one embodiment, the portable $SpO_2$ sensor may be a CheckMate™ portable finger pulse oximeter available from SPO Medical.

Such a pulse oximeter is generally configured to indirectly (or non-invasively) measure the oxygen saturation of the patient's blood. In other words, the pulse oximeter is configured to monitor the percentage of hemoglobin (Hb) which is saturated with oxygen. In one embodiment, the pulse oximeter may include a probe attached to patient's finger or patient's ear lobe.

Heart rate monitor 208 is configured to detect heart beat of the patient such that a signal from the heart rate monitor is correlated to the patient's heart rate. In one embodiment, heart rate monitor 208 is electronic and electronically inputs the heart rate data into processor 214.

In one embodiment, heart rate monitor 208 may include a wearable heart rate monitor (e.g., Polar F7 heart rate monitor watch) available from Polar. In one embodiment, the heart rate monitor may include a built in microprocessor that analyzes an EKG signal to determine the heart rate of the patient. In one embodiment, the heart rate monitor may include a transmitter located at the position where the patient's heart is located so as to detect the patient's heartbeat and a receiver located, for example, on patient's wrist.

In one embodiment, heart rate monitor 208 may be directly connected to the processor 214. In such an embodiment, the heart rate monitor 208 may be connected to the processor 214 over a wired or wireless network, for example. It is also contemplated that the heart rate monitor 208 may be connected to processor 214 via the data storage device 216.

In one embodiment, the volume of air inspired by or exhaled by the lungs is measured using airway obstruction measuring device 212. In one embodiment, the airway obstruction measuring device may include a spirometer. In one embodiment, the spirometer is a handheld spirometer. For example, in one embodiment, the handheld spirometer may be a MicroGP spirometer available from Micro Direct, Inc. In one embodiment, the spirometer may include an analog spirometer or a digital spirometer.

In one embodiment, the airway obstruction is assessed using a spirometry test. During the spirometry test, patient breathes into a mouth piece that is connected to a spirometer. The spirometer is configured to record the amount and the rate of air that patient breathes in and out over a period of time. In one embodiment, during the spirometry test, the patient takes the deepest breath they can and exhales as hard as possible for as long as they are able to. In one embodiment, the spirometry test is normally repeated three times to ensure reproducibility.

The spirometer measures Forced Expiratory Volume measured over one second ($FEV_1$) (i.e., volume expired in the first second of maximal expiration after a maximal inspiration). $FEV_1$ is a measure of how quickly the lungs can be emptied. A lower $FEV_1$ value generally indicates a greater degree of airway obstruction.

The spirometer is also configured to measure Forced Vital Capacity (FVC) (i.e., maximum volume of air that can be exhaled during a forced maneuver), and Peak Expiratory Flow (PEF). The spirometer is also configured to measure $FEV_1/FVC$ (i.e., $FEV_1$ expressed as a percentage of the FVC). $FEV_1/FVC$ provides a clinically useful index of airflow limitation. For example, a value of $FEV_1/FVC$ less than 70% indicates airflow limitation and the possibility of COPD.

The airway obstruction grading is illustrated in the TABLE. 2. TABLE. 2 shows the $FEV_1$ as a percentage of a predicted value. The predicted value is determined based on patient's age, patient's sex, patient's height, patient's weight, and/or patient's race.

TABLE 2

| Mild airway obstruction | Moderate airway obstruction | Severe airway obstruction | Very severe airway obstruction |
| --- | --- | --- | --- |
| $FEV_1 \geq 80\%$ of a predicted value | 50% of a predicted value $\leq FEV_1 < 80\%$ of a predicted value | 30% of a predicted value $\leq FEV_1 < 50\%$ of a predicted value | $FEV_1 < 30\%$ of a predicted value |

If the measured $FEV_1$ value is greater than 80% of the predicted value, then the patient may have a mild airway obstruction. If the measured $FEV_1$ value is between 50% of a predicted value and 80% of a predicted value, then the patient may have a moderate airway obstruction. If the measured $FEV_1$ value is between 30% of a predicted value and 50% of a predicted value, then the patient may have a severe airway obstruction. If the measured $FEV_1$ value is less than 30% of a predicted value, then the patient may have a very severe airway obstruction.

In another embodiment, airway obstruction device 212 may include a peak flow meter. The peak flow meter is configured to measure the patient's maximum speed of expiration, or peak expiratory flow (PEFR or PEF). The peak flow readings are higher when patient's airways are not constricted, and lower when the patient's airways are constricted.

The spirometer and the peak flow meter described above are just two examples for measuring the airway obstruction data, however, it is contemplated that other airway obstruction measuring devices known in the art may be used to measure the airway obstruction data of the patient. In a further embodiment, the spirometer is not worn by the patient during the exercise training.

In one embodiment airway obstruction device 212 may be directly connected to processor 214. In such an embodiment, the airway obstruction device may be connected to the processor over a wired or wireless network, for example. It is also contemplated that airway obstruction device 212 may be connected to processor 214 via data storage device 216.

In one embodiment, temperature sensor 210 is used to monitor the body temperature of the patient. In one embodiment, the temperature sensor may be in the form of a patch that is attached to the patient's body. In one embodiment, for improved accuracy (e.g., for accuracy of 0.3° C. or more), temperature sensor 210 may generally be placed in the forehead region of the patient. In an alternative embodiment, the temperature sensor may generally be placed in chest/abdominal region of the patient. In such an embodiment, temperature sensor 210 is constructed and arranged to have a larger surface area.

In one embodiment, the core body temperature sensor may be in the form of a sensor described in these European Patent Nos.: 06126697.9; 06125479.3; 08156802.4; 09157392.3; and 09155065.7; and U.S. Patent Application Ser. Nos. 60/894,915 60/894,916; 60/894,917; 61/032,084 and 61/145,605, the contents of each of which is hereby incorporated by reference.

In one embodiment, exercise equipment 220 may include a weight training device and/or cardiovascular exercise device. In one embodiment, the cardiovascular exercise device may include a treadmill, an elliptical trainer, a rowing machine, a stationary bicycle, a stair climber, a stepper, a pilates machine, an aerobic rider or flyer, and/or any other suitable cardiovascular exercise device. In one embodiment, exercise equipment/device 220 may be directly connected to processor 214. In such an embodiment, the exercise equipment/device may be connected to the processor over a wired or wireless network, for example.

As noted above, in one embodiment, exercise equipment/device 220 may be configured to send the signal to processor 214 that the (devised) exercise training plan of the patient is complete. In one embodiment, the processor may be configured to send signals to the exercise equipment/device to modify the exercise training plan for the patient.

In one embodiment, system 200 may include user interface 218, which is in communication with processor 214 and/or data storage device 216. The user interface is configured to accept input from the patient (or caregiver), and optionally to transmit (and display) output of system 200.

In one embodiment, user interface 218 may include a keypad that allows the patient or caregiver to the health information data into processor 214. Such the health information data may include, for example, patient's information (i.e., patient's gender, patient's age, patient's weight, patient's smoking history, and patient's height), and/or patient's symptoms (i.e., dyspnea (or shortness of breath), cough, wheezing, mucus or sputum production, chest tightness, and fatigue). In one embodiment, the patient or the caregiver may input the volume of air inspired by or exhaled by the lungs (obtained from spirometer 212) into processor 214 using user interface 218.

In one embodiment, user interface 218 may include a display screen that provides a visual data output (e.g., the assessed health status of the patient) to the patient. In one embodiment, the user interface may be a graphical user interface. It may also include a printer or be connected to a printer so as to be able to print information from processor 214.

In one embodiment, user interface 218 may be provided integral with the sensor set (i.e., the activity monitor, the respiration rate sensor, the $SpO_2$ sensor, heart rate monitor, and/or temperature sensor). In another embodiment, the user interface may be provided remote from or proximal to the sensor set.

In one embodiment, system 200 may include the data storage unit or memory 216, which is in communication with processor 214 and/or user interface 218. In system 200 shown in FIG. 2, data storage unit or memory 216 is a standalone device. However, it is contemplated that data storage unit or memory 216 may be part of processor 214. In one embodiment, the data storage unit or memory is configured to receive data from all the sensors (i.e., the activity monitor, the respiration rate sensor, the $SpO_2$ sensor, heart rate monitor, and/or temperature sensor) that are monitoring the physiological parameters of the patient.

In one embodiment, data storage unit or memory 216 is constructed and arranged to receive (via user interface 218) and store the health information data input by the patient (or caregiver). As noted above, such health information data may include, for example, patient's information (i.e., patient's gender, patient's age, patient's weight, patient's smoking history, and patient's height), and/or patient's symptoms (i.e., dyspnea (or shortness of breath), cough, wheezing, mucus or sputum production, chest tightness, and fatigue). In one embodiment, the volume of air inspired by or exhaled by the lungs is input by the patient (or caregiver) into data storage unit or memory 216.

In one embodiment, processor 214 is configured to receive the health information data, and the volume of air inspired by or exhaled by the lungs stored in data storage device (or memory) 216. As noted above, this health information data, and the volume of air inspired by or exhaled by the lungs along with the physiological data from the sensors (i.e., the activity monitor, the respiration rate sensor, the $SpO_2$ sensor, heart rate monitor, and/or temperature sensor) are used to device the exercise training plan for the patient.

In one embodiment, the stored data in data storage unit or memory 216 may also be used for further processing, for example, for trending, and/or display.

In one embodiment, method 100 and system 200 may be configured to use the physiological data for guiding the education component and the nutritional component of the pulmonary rehabilitation. For example, in one embodiment, if the patient has problems with dyspnea, method 100 and system 200 may be configured to educate the patient on breathing exercises. In one embodiment, if the patient is underweight, method 100 and system 200 may be configured to educate the patient on nutrition. In one embodiment, based on the type of the exercise training (e.g., aerobics, muscle strength training) provided to the patient, method 100 and system 200 may be configured to educate the patient on nutrition.

In one embodiment, method 100 and system 200 may be used in a rehabilitation center (e.g., for COPD patients, stroke patients, or heart failure patients). In one embodiment, method 100 and system 200 may also be applied for home rehabilitation to enable patient assessment, training guidance and intervention to be provided remotely.

In one embodiment, the physiological data may offer a continuous feedback for a rehabilitation team to modify/adjust the exercise training session based on an improvement or worsening of the patient's physiological data. The continuous feedback may include a comparison of the patient's current physiological data to the patient's physiological data measured during the previous exercise training sessions. In one embodiment, a comparison of previous data with current data (e.g., using % changes) will provide information on patient progress, which may lead to a modification in the exercise training program (i.e., either an increase or a decrease in program intensity, duration, type of exercises, etc.).

In one embodiment, system 200 may each include a single processor configured to provide an exercise training plan for a patient. In another embodiment, the system may include multiple processors, where each processor is configured to perform a specific function or operation. In such an embodiment, the multiple processors may be configured to provide an exercise training plan for a patient.

Embodiments of the invention, such as the processor, for example, may be made in hardware, firmware, software, or various combinations thereof. The invention may also be implemented as instructions stored on a machine-readable medium, which may be read and executed using one or more processors. In one embodiment, the machine-readable medium may include various mechanisms for storing and/or transmitting information in a form that can be read by a machine (e.g., a computing device). For example, a machine-readable storage medium may include read only memory, random access memory, magnetic disk storage media, optical storage media, flash memory devices, and other media for storing information, and a machine-readable transmission media may include forms of propagated signals, including carrier waves, infrared signals, digital signals, and other media for transmitting information. While firmware, software, routines, or instructions may be described in the above disclosure in terms of specific exemplary aspects and embodiments performing certain actions, it will be apparent that such descriptions are merely for the sake of convenience and that such actions in fact result from computing devices, processing devices, processors, controllers, or other devices or machines executing the firmware, software, routines, or instructions.

Although the invention has been described in detail for the purpose of illustration, it is to be understood that such detail is solely for that purpose and that the invention is not limited to the disclosed embodiments, but, on the contrary, is intended to cover modifications and equivalent arrangements that are within the spirit and scope of the appended claims. In addition, it is to be understood that the present invention contemplates that, to the extent possible, one or more features of any embodiment can be combined with one or more features of any other embodiment.

What is claimed is:

1. An exercise system comprising:
a sensor configured to generate output signals conveying information related to physiological data from the patient, wherein the physiological data comprises a forced expiratory volume, a forced vital capacity, and a peak expiratory flow; and
a physical computer processor operatively connected to the sensor configured by computer readable instructions to:
a) receive health information data from the patient via a user interface of a computing device associated with the patient, the health information data representative of patient information and/or patient symptoms,
b) receive the physiological data from the sensor,
c) devise an exercise training plan for the patient based on the health information data and the physiological data,
d) monitor the physiological data during exercise training of the patient to determine if the physiological data is within a predetermined range, and
e) modify an intensity and/or a duration of the exercise training plan for the patient responsive to one or more of the forced expiratory volume, the forced vital capacity, or the peak expiratory flow being outside the predetermined range.

2. The system of claim 1, wherein the processor is further configured to measure the physiological data after the exercise training of the patient and to determine if the physiological data after the exercise training is within the predetermined range.

3. The system of claim 2, wherein the processor is further configured to modify the exercise training plan for the patient if the physiological data is outside the predetermined range.

4. The system of claim 1, wherein the patient information comprises one or more of the patient's gender, age, weight, smoking history, or height.

5. The system of claim 1, wherein the patient symptoms comprise one or more of dyspnea, cough, wheezing, mucus or sputum production, chest tightness, or fatigue.

6. The system of claim 1, wherein the physiological data further comprises additional physiological data, the additional physiological data comprising one or more of physical activity data, respiration rate data, heart rate data, body temperature data, or $SpO2$ data.

7. The system of claim 6, wherein modification of the exercise training plan for the patient is further based on the additional physiological data.

8. The system of claim 1, wherein the sensor includes a spirometer and a peak flow meter and the output signals are generated using the spirometer and the peak flow meter.

9. The system of claim 1, wherein:
the sensor is a sensor set including an activity monitor, a respiration rate sensor, an $SpO_2$ sensor, a heart rate monitor, a temperature sensor, and an airway obstruction device;
the physiological data comprises the forced expiratory volume, the forced vital capacity, the peak expiratory flow, a body temperature, a heart rate, a level of $SpO_2$, a respiration rate, and a physical activity level; and
the processor is configured to modify the intensity and/or duration of the exercise training plan for the patient responsive to one or more of the forced expiratory volume, the forced vital capacity, the peak expiratory flow, the body temperature, the heart rate, the level of SpO$_2$, the respiration rate, or the physical activity level being outside the predetermined range.

10. A method implemented with an exercise system comprising a physical computer processor configured to execute computer readable instructions and a sensor, the method comprising:
  generating, with the sensor, output signals conveying information related to physiological data from the patient, wherein the physiological data comprises a forced expiratory volume, a forced vital capacity, and a peak expiratory flow;
  receiving health information data from the patient via a user interface of a computing device associated with the patient, the health information data representative of patient information and/or patient symptoms;
  devising an exercise training plan for the patient based on the health information data and the physiological data;
  monitoring the physiological data during exercise training of the patient to determine if the physiological data are within a predetermined range; and
  modifying an intensity and/or a duration of the exercise training plan for the patient responsive to one or more of the forced expiratory volume, the forced vital capacity, or the peak expiratory flow being outside the predetermined range.

11. The method of claim 10, further comprising monitoring the physiological data after the exercise training of the patient to determine if the physiological data are within the predetermined range.

12. The method of claim 11, further comprising modifying the exercise training plan for the patient if the physiological data is outside the predetermined range.

13. The method of claim 10, wherein the patient information comprises one or more of the patient's gender, age, weight, smoking history, or height.

14. The method of claim 10, wherein the physiological data further comprises additional physiological data, the additional physiological data comprising one or more of physical activity data, respiration rate data, heart rate data, body temperature data, or SpO$_2$ data.

15. The method of claim 14, wherein modification of the exercise training plan for the patient is further based on the additional physiological data.

16. The method of claim 10, wherein the sensor includes a spirometer and a peak flow meter and the output signals are generated using the spirometer and the peak flow meter.

17. The method of claim 10, wherein:
  the sensor is a sensor set including an activity monitor, a respiration rate sensor, an SpO$_2$ sensor, a heart rate monitor, a temperature sensor, and an airway obstruction device;
  the physiological data comprises the forced expiratory volume, the forced vital capacity, the peak expiratory flow, a body temperature, a heart rate, a level of SpO$_2$, a respiration rate, and a physical activity level; and
  modifying the intensity and/or duration of the exercise training plan for the patient includes modifying the intensity and/or duration responsive to one or more of the forced expiratory volume, the forced vital capacity, the peak expiratory flow, the body temperature, the heart rate, the level of SpO$_2$, the respiration rate, or the physical activity level being outside the predetermined range.

* * * * *